(12) United States Patent
Zhang et al.

(10) Patent No.: US 9,527,804 B2
(45) Date of Patent: Dec. 27, 2016

(54) 4-BENZYL-1-PHENETHYL-PIPERAZINE-2,6-DIONE PREPARATION METHOD, AND INTERMEDIATE AND PREPARATION METHOD THEREOF

(71) Applicants: Zhejiang Hisun Pharmaceutical Co., Ltd., Taizhou (CN); Shanghai Institute of Pharmaceutical Industry, Shanghai (CN)

(72) Inventors: Fuli Zhang, Shanghai (CN); Zhezhou Yang, Shanghai (CN); Rusheng Bao, Taizhou (CN); Pengcheng Qiu, Shanghai (CN); Linyong Jin, Shanghai (CN); Hu Pan, Shanghai (CN); Linyu Pan, Shanghai (CN); Dongming Jiang, Taizhou (CN); Weiwei Xu, Taizhou (CN)

(73) Assignees: Zhejiang Hisun Pharmaceutical Co., Ltd. (CN); Shanghai Institute of Pharmaceutical Industry (CN)

( * ) Notice: Subject to any disclaimer, the term of this patent is extended or adjusted under 35 U.S.C. 154(b) by 0 days.

(21) Appl. No.: 14/899,350

(22) PCT Filed: Jun. 23, 2014

(86) PCT No.: PCT/CN2014/080498
§ 371 (c)(1),
(2) Date: Dec. 17, 2015

(87) PCT Pub. No.: WO2014/206254
PCT Pub. Date: Dec. 31, 2014

(65) Prior Publication Data
US 2016/0130218 A1    May 12, 2016

(30) Foreign Application Priority Data
Jun. 24, 2013   (CN) .......................... 2013 1 0255096

(51) Int. Cl.
*C07D 241/04*     (2006.01)
*C07C 231/02*     (2006.01)
(Continued)

(52) U.S. Cl.
CPC ........... *C07C 237/06* (2013.01); *C07C 231/02* (2013.01); *C07C 231/10* (2013.01); *C07D 241/08* (2013.01); *C07D 471/04* (2013.01)

(58) Field of Classification Search
CPC ... C07D 241/08; C07D 471/04; C07C 231/10; C07C 237/06; C07C 231/02
(Continued)

(56) References Cited
U.S. PATENT DOCUMENTS
2009/0105269 A1    4/2009    Kador et al.

FOREIGN PATENT DOCUMENTS
WO    2011107948 A2    9/2011

OTHER PUBLICATIONS

Henry, D. W., "A Facile Synthesis of Piperazines from Primary Amines (1)", Journal of Heterocyclic Chemistry, pp. 503-511, vol. 3, Dec. 31, 1966, ISSN: see the whole document.
(Continued)

*Primary Examiner* — T. Victor Oh
(74) *Attorney, Agent, or Firm* — Lerner, David, Littenberg, Krumholz & Mentlik, LLP

(57) ABSTRACT

The present invention provides a key new intermediate (a compound of formula III) of 4-benzyl-1-phenethyl-piperazine-2,6-dione (formula IV compound), a pharmaceutically acceptable salt thereof and a preparation method thereof. The present invention additionally discloses a method for preparing 4-benzyl-1-phenethyl-piperazine-2,6-dione (formula IV compound) from the formula III compound, said method overcoming the shortcomings of current formula IV compound preparation methods, such as low production volumes, low purity, high energy consumption, high costs, and inability to achieve industrialized production, and provides a formula IV compound preparation method which is simple, economical, environmentally-friendly and easy to produce industrially; the reaction solvent of the method is easily recycled and the method can produce the formula IV compound at high production rates and with high purity.

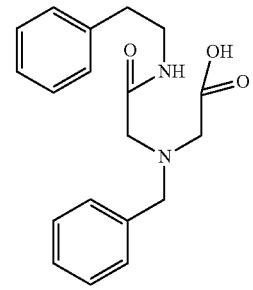

III

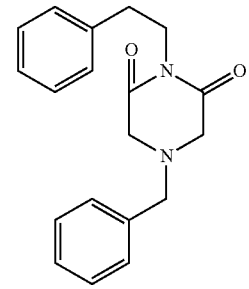

IV

11 Claims, No Drawings

(51) Int. Cl.
*C07C 237/06* (2006.01)
*C07D 241/08* (2006.01)
*C07D 471/04* (2006.01)
*C07C 231/10* (2006.01)

(58) Field of Classification Search
USPC .......................... 549/464; 544/385; 562/450
See application file for complete search history.

(56) References Cited

OTHER PUBLICATIONS

Yuste, F. et al., "A Short Synthesis of Praziquantel", Journal of Heterocyclic Chemistry, No. 1, vol. 23, Dec. 31, 1986, ISSN: pp. 189-190, see the whole document.

Brewer, M.D. et al., "Synthesis and Anthelmintic Activity of a Series of Pyrazino [2, 1-A] [2] Benzazepine Derivatives", Journal of Medicinal Chemistry, No. 9, vol. 32, Dec. 31, 1989, ISSN: pp. 2058-2062, see the whole document.

International Search Report for Application No. PCT/CN2014/080498 dated Sep. 30, 2014.

Design, synthesis and molecular modeling study of iminodiacetyl monohydroxamic acid derivatives as MMP inhibitors, M. Amelia Santos etal, Bioorganic & Medicinal Chemistry 14 (2006) 7539-7550.

Chinese Search Report for Application No. 2013102550961 dated May 28, 2015.

4-BENZYL-1-PHENETHYL-PIPERAZINE-2,6-DIONE PREPARATION METHOD, AND INTERMEDIATE AND PREPARATION METHOD THEREOF

CROSS-REFERENCE TO RELATED APPLICATIONS

The present application is a national phase entry under 35 U.S.C §371 of International Application No. PCT/CN2014/080498 filed Jun. 23, 2014, published as WO 2014/206254, which claims priority from Chinese Application No. 201310255096.1 filed Jun. 24, 2013, all of which are hereby incorporated herein by reference.

FIELD OF THE INVENTION

The present invention relates to pharmacy field. More specifically, the present invention relates to a method for preparing 4-benzyl-1-phenethyl-piperazine-2,6-dione (a compound of formula IV), an intermediate of schistosomicide praziquantel. The present invention further relates to a new key intermediate (a compound of formula III) of the compound of formula IV and the preparation method thereof, as well as use of the compound in the preparation of schistosomicide praziquantel.

BACKGROUND OF THE INVENTION

Praziquantel is a broad spectrum insecticide, and is especially suitable for the treatment of acute and chronic schistosomiasis along with complications, which is a choice drug for treating schistosomiasis at present. The structural formula of praziquantel is formula V as below:

V

Francisco Yuste et al. (Journal of Heterocyclic Chemistry, 1986, Vol. 23, p 189-190.) discloses a method for preparing praziquantel with the following reaction scheme, wherein the key intermediate compound of formula IV was subjected to many reaction steps to obtain the praziquantel compound of formula V.

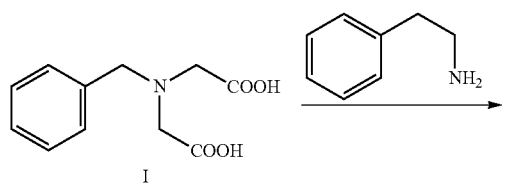

I

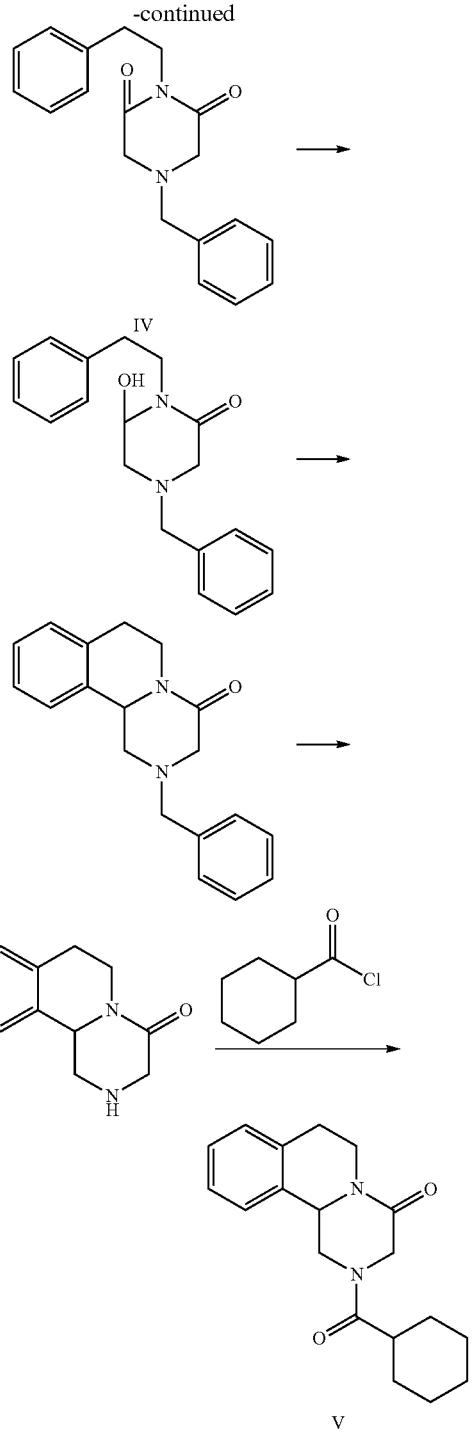

As to the key intermediate 4-benzyl-1-phenethyl-piperazine-2,6-dione (the compound of formula IV) in the above reaction, Francisco Yuste et al. (Journal of Heterocyclic Chemistry, 1986, Vol. 23, p 189-190.) and Malcolm D. Brewer et al. (Journal of Medicinal Chemistry, 1989, Vol. 32, No. 9, p 2058-2062.) disclose a method for preparing this compound.

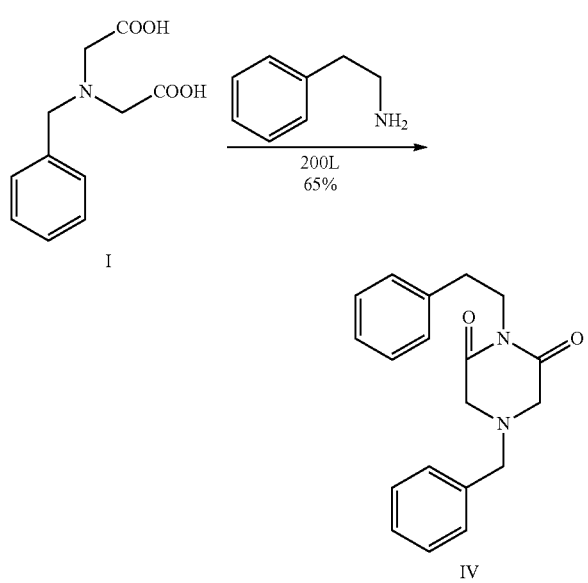

As disclosed in the method, the compound of formula I was directly mixed with β-phenethylamine and heated to 200° C., to obtain the compound of formula IV at a yield of 65%. This method has a low yield and produces many impurities, thus the product is hard to purify. Meanwhile, the high-temperature reaction not only is energy-consuming, but also has a high requirement on the device, which is hard to achieve industrial production.

In view of the importance of the compound of formula IV in synthesizing praziquantel compound of formula V, it is greatly meaningful to develop a preparation method having high yield, high purity and being easily applicable in industrial production.

SUMMARY OF THE INVENTION

The present invention provides a new key intermediate (a compound of formula III) for synthesizing the schistosomicide, or pharmaceutically acceptable salts thereof.

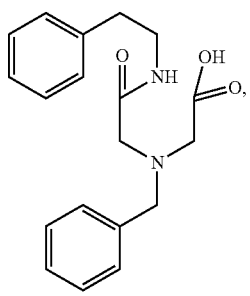

wherein, the pharmaceutically acceptable salts of the compound of formula III may be sulfates, hydrochlorides, phosphates, acetates, oxalates, formates, nitrates or mesylates.

The present invention further provides a method for preparing the compound of formula III comprising the reaction steps of:

Step 1. carrying out a dehydration reaction between a compound of formula I and acetic anhydride

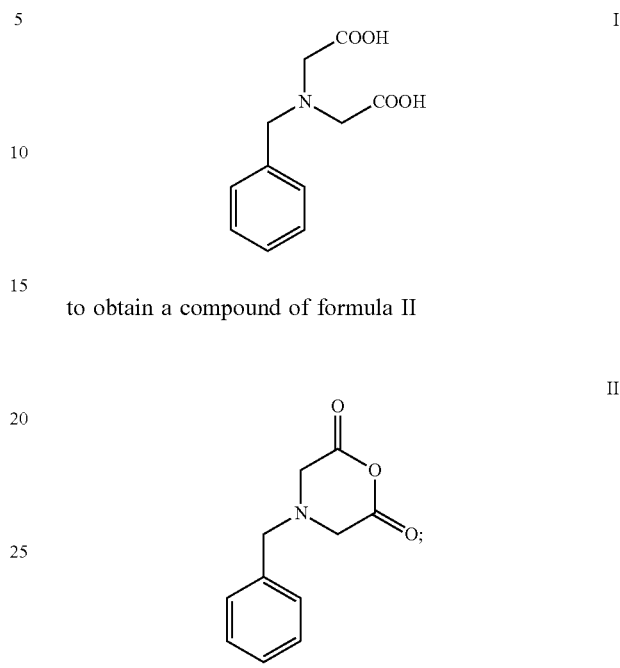

to obtain a compound of formula II

Step 2. carrying out an acylation reaction between the compound of formula II and β-phenethylamine with the presence of an aprotic organic solvent or without a solvent, to obtain the compound of formula III.

In the above reaction step 1, the compound of formula II can be prepared from a compound of formula I by the method according to the literature (US2009105269; Journal of Heterocyclic Chemistry; vol. 3; 1966; p. 503-511).

The aprotic organic solvents in step 2 are selected from ether, aromatic hydrocarbon, hydrocarbon or halogenated hydrocarbon, ester and ketone solvents.

Further, the above ether solvents are selected from tetrahydrofuran, ethyl ether, 1,2-dimethoxyethane, methyl tert-butyl ether and 2-methyl tetrahydrofuran; the aromatic hydrocarbon solvents are selected from benzene, toluene, ethylbenzene and dimethylbenzene; the hydrocarbon or halogenated hydrocarbon solvents are selected from n-hexane, cyclohexane, n-heptane, dichloromethane, trichloromethane and dichloroethane; the ester solvents are selected from methyl formate, ethyl formate, methyl acetate, ethyl acetate and isopropyl acetate; and the ketone solvents are selected from acetone, butanone and methyl isobutyl ketone.

Further, the aprotic organic solvents are preferably methyl tert-butyl ether, acetone, toluene, ethyl acetate or isopropyl acetate.

In step 2, the temperature of the acylation reaction is 0-100° C., preferably 5-40° C., more preferably room temperature.

The present invention further relates to a method for preparing the key intermediate of praziquantel with the following formula IV, comprising carrying out a cyclization reaction of the compound of formula III in the presence of a dehydrating agent and an alkaline substance in an aprotic organic solvent or without a solvent, to obtain the compound of formula IV as follow:

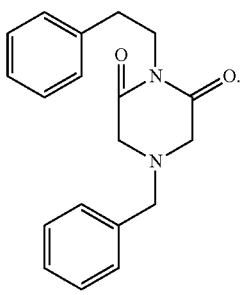

The dehydrating agents in the cyclization reaction are selected from one or more substances of acetic anhydride, propionic anhydride, trifluoroacetic anhydride, acetyl chloride, propionyl chloride, chloroacetyl chloride, oxalyl chloride, phosgene and triphosgene, preferably acetic anhydride.

The alkaline substances in the cyclization reaction are selected from one or more substances of triethylamine, imidazole, pyridine, 2-methylpyridine, 2,6-dimethylpyridine, 4-dimethylaminopyridine, piperidine, 1-methylpiperidine, morpholine, 4-methylmorpholine, quinoline, 1-methylpyrrolidine, diisopropylamine, dimethylisopropylamine, di(isopropyl)ethylamine and sodium acetate, preferably triethylamine.

The aprotic organic solvents in the cyclization reaction are selected from ether, aromatic hydrocarbon, hydrocarbon or halogenated hydrocarbon, ester and ketone solvents.

Further, the above ether solvents are selected from tetrahydrofuran, ethyl ether, 1,2-dimethoxyethane, methyl tert-butyl ether and 2-methyltetrahydrofuran; the aromatic hydrocarbon solvents are selected from benzene, toluene, ethylbenzene and dimethylbenzene; the hydrocarbon or halogenated hydrocarbon solvents are selected from n-hexane, cyclohexane, n-heptane, dichloromethane, trichloromethane and dichloroethane; the ester solvents are selected from methyl formate, ethyl formate, methyl acetate, ethyl acetate and isopropyl acetate; and the ketone solvents are selected from acetone, butanone and methyl isobutyl ketone.

Further, the aprotic organic solvents in the cyclization reaction are preferably methyl tert-butyl ether, acetone, toluene, ethyl acetate or isopropyl acetate.

The temperature of the cyclization reaction is 0-100° C., preferably 40-80° C.

Another object of the present invention is to provide pharmaceutical acceptable salts of the compound of formula III, which can be prepared by the method as below: the compound of formula III was subjected to salt forming reaction in the presence of acid aqueous solution to obtain the pharmaceutical acceptable salts of the compound of formula III.

The acid aqueous solutions can be selected from sulfuric acid, hydrochloric acid, phosphoric acid, acetic acid, oxalic acid, formic acid, nitric acid and methanesulfonic acid aqueous solutions.

The present invention further relates to a method for preparing the compound of formula IV from the pharmaceutical acceptable salt of the compound of formula III: carrying out a cyclization reaction of the pharmaceutical acceptable salt of the compound of formula III in the presence of an alkaline substance and a dehydrating agent, to obtain the compound of formula IV, wherein the alkaline substance and the dehydrating agent are as defined above.

The present invention further relates to use of the compound of formula III and the pharmaceutical acceptable salts thereof and the compound of formula IV in the preparation of schistosomicide praziquantel.

The design of synthetic process for preparing 4-benzyl-1-phenethyl-piperazine-2,6-dione (the compound of formula IV) is reasonable, economic and environmental. Additionally, the source of the raw materials is convenient, and the product has a high total yield (≥91%). Furthermore, the compound of formula IV has a high chemical purity (the HPLC purity is more than 98%) and is easy to achieve industrial mass production.

The methods of the present invention overcome the shortcomings of current methods for preparing the compounds of formula IV, such as low production volumes, low purity, high energy consumption, high costs, and inability to achieve industrialized production, and provides a method for preparing the compound of formula IV, which is economical, environmental and easy to achieve industrialized production. In the present invention, the reaction solvent of the method is easily recycled and the method can produce the compound of formula IV at a high yield and with a high purity.

DETAILED DESCRIPTION OF EMBODIMENTS

The present invention will be further described in combination with the following Examples, however, these Examples will not limit the scope of the present invention.

$^1$HNMR is recorded by AM 400 Type Nuclear Magnetic Resonance Spectrometer, and the chemical shift is represented as δ (ppm). Mass spectrum is determined by Shimadzu LCMS-2010 mass spectrometer.

Example 1

The Preparation of 2-{benzyl[2-(phenethylamino)-2-oxo-ethyl]amino}acetic acid (the Compound of Formula III)

To a 250 ml reaction flask 10.0 g N-benzyliminodiacetic acid (the compound of formula I) and 35.0 g acetic anhydride were added in sequence, reacted at 90-100° C. for 30 min, and then cooled. The reaction mixture was distilled under reduced pressure to remove the acetic acid and acetic anhydride, to obtain a dark red oily substance. The obtained dark red oily substance was cooled in ice bath, and then a mixture of 5.5 g β-phenethylamine and 150 ml acetone was added dropwise. After dropping, the ice bath was removed, and the reaction mixture was reacted at room temperature for 2 h, solid is precipitated. Solvent was removed under reduced pressure, to result 14.40 g light yellow solid (yield: 98.5%).

$^1$H-NMR (CD$_3$OD) δ: 2.81 (t, 2H), 3.50 (q, 2H), 3.99 (s, 2H), 4.10 (s, 2H), 4.46 (s, 2H), 7.20~7.30 (m, 5H), 7.51 (m, 5H), 8.38 (t, 1H); MS(ESI) m/z: 327.17 (M+1).

Example 2

The Preparation of 2-{benzyl[2-(phenethylamino)-2-oxo-ethyl]amino}acetic acid hydrochloride (a Hydrochloride of the Compound of Formula III)

To a 250 ml reaction flask 10.0 g N-benzyliminodiacetic acid (the compound of formula I) and 35.0 g acetic anhydride were added in sequence, reacted at 90-100° C. for 30 min, and then cooled. The reaction mixture was distilled under reduced pressure to remove the acetic acid and acetic anhydride, to obtain a dark red oily substance. The obtained dark red oily substance was cooled in ice bath, and then a mixture of 5.5 g β-phenethylamine and 150 ml acetone was added dropwise. After dropping, the ice bath was removed, and the reaction mixture was reacted at room temperature for 2 h, and then 25 ml 10% dilute hydrochloric acid was added and stirred for 0.5 h. Solvent was removed under reduced pressure, to obtain 16.12 g white solid (yield: 99.2%).

Example 3

The Preparation of 2-{benzyl[2-(phenethylamino)-2-oxo-ethyl]amino}acetic acid sulfate (a Sulfate of the Compound of Formula III)

To a 250 ml reaction flask 10.0 g N-benzyliminodiacetic acid (the compound of formula I) and 35.0 g acetic anhydride were added in sequence, reacted at 90-100° C. for 30 min, and then cooled. The reaction mixture was distilled under reduced pressure to remove the acetic acid and acetic anhydride, to obtain a dark red oily substance. The obtained dark red oily substance was cooled in ice bath, and then a mixture of 5.5 g β-phenethylamine and 150 ml acetone was added dropwise. After dropping, the ice bath was removed, and the reaction mixture was reacted at room temperature for 2 h, and then 25 ml 10% dilute sulphuric acid was added and stirred for 0.5 h. Solvent was removed under reduced pressure, to obtain 18.92 g white solid (yield: 99.5%).

Example 4

The Preparation of 4-benzyl-1-phenethyl-piperazine-2,6-dione (the Compound of Formula IV)

To a 250 ml reaction flask 6.35 g N-benzyliminodiacetic acid (the compound of formula I) and 23.30 g acetic anhydride were added in sequence, reacted at 120-130° C. for 20 min, and then cooled. The reaction mixture was distilled under reduced pressure to remove the acetic anhydride, to obtain a dark red oily substance. To the obtained dark red oily substance 80 ml methyl tert-butyl ether was added and then 3.44 g β-phenethylamine was added dropwise. After dropping, the reaction mixture was reacted at room temperature for 4 h. To the reaction mixture 14.76 g acetic anhydride, 2.90 g triethylamine and 1.10 g sodium acetate were further added in sequence, and then reacted under reflux for 4 h. The reaction solution was cooled and 150 ml water was added. Then the reaction solution was adjusted with NaOH aqueous solution until pH=7~8. The water layer was separated. Then the separated water layer was extracted with 50 ml methyl tert-butyl ether, and the organic phase was washed with 40 ml water twice, and Dried with anhydrous magnesium sulfate, filtered and concentrated, obtaining a dark red oily substance. The obtained dark red oily substance was recrystallized by methanol to obtain 8.10 g solid (yield: 92.3%, HPLC purity: 98.5%, mp 78.3~78.5° C.).

$^1$H-NMR (CDCl$_3$) δ: 2.85 (m, 2H), 3.37 (s, 4H), 3.58 (s, 2H), 3.99 (m, 2H), 7.25 (m, 5H), 7.31 (m, 5H); MS(ESI) m/z: 309.16 (M+1).

Example 5

The Preparation of 4-benzyl-1-phenethyl-piperazine-2,6-dione (the Compound of Formula IV)

To a 250 ml reaction flask 6.5 g N-benzyliminodiacetic acid (the compound of formula I) and 23.30 g acetic anhydride were added in sequence, reacted at 120-130° C. for 20 min, and then cooled. The reaction mixture was distilled under reduced pressure to remove the acetic anhydride, to obtain a dark red oily substance. To the obtained dark red oily substance 150 ml acetone was added and then 3.53 g β-phenethylamine was added dropwise. After dropping, the reaction mixture was stirred at room temperature for 1 h. To the reaction mixture 15.08 g acetic anhydride and 3.90 g di(isopropyl)ethylamine were further added in sequence, and then reacted under reflux for 4 h. The reaction mixture was cooled and concentrated, and then 100 ml ethyl acetate and 100 ml water were added to the residue. Stirred until layering, the organic phase was washed with 40 ml water twice, and dried with anhydrous magnesium sulfate, filtered and concentrated, obtaining a yellow oily substance. The obtained yellow oily substance was recrystallized by methanol to obtain 8.33 g solid (yield: 92.8%, HPLC purity: 98.7%).

Example 6

The Preparation of 4-benzyl-1-phenethyl-piperazine-2,6-dione (the Compound of Formula IV)

To a 250 ml reaction flask 10.05 g N-benzyliminodiacetic acid (the compound of formula I) and 35.0 g acetic anhydride were added in sequence, reacted at 90-100° C. for 15 min, and then cooled. The reaction mixture was distilled under reduced pressure to remove the acetic acid and acetic anhydride, to obtain a dark red oily substance. The obtained dark red oily substance was cooled in ice bath, and then a mixture of 5.5 g β-phenethylamine and 150 ml isopropyl acetate was added dropwise. After dropping, the ice bath was removed, and the reaction mixture was reacted at room temperature for 1 h. To the reaction mixture 11.5 g acetic anhydride and 5.0 g triethylamine were further added in sequence, and then reacted at 60° C. for 4 h. The reaction solution was cooled and 50 ml water was added. Then the reaction solution was adjusted with potassium carbonate until pH was about 8. The water layer was separated. Then the separated water layer was extracted with 50 ml isopropyl acetate, and the organic phase was combined and washed with 50 ml water twice, and then concentrated to obtain a dark red oily substance. The obtained dark red oily substance was recrystallized by methanol to obtain 12.77 g solid (yield: 92.0%, HPLC purity: 99.3%).

Example 7

The Preparation of 4-benzyl-1-phenethyl-piperazine-2,6-dione (the Compound of Formula IV)

To a 1 L reaction flask 60 g N-benzyliminodiacetic acid (the compound of formula I) and 210 g acetic anhydride were added in sequence, reacted at 90-100° C. for 40 min, and then cooled. The reaction mixture was distilled under reduced pressure to remove the acetic acid and acetic anhydride, to obtain a dark red oily substance. To the obtained dark red oily substance 360 ml acetone was added and cooled in ice bath, and then 33 g β-phenethylamine was added dropwise. After dropping, the ice bath was removed, and the reaction mixture was reacted at room temperature for 2 h. To the reaction mixture 110 g acetic anhydride and 33 g triethylamine were further added in sequence, and then reacted under reflux for 4 h. The reaction mixture was cooled and concentrated, and then 150 ml water and 350 ml ethyl acetate were added to the residue. The reaction solution was adjusted with NaOH aqueous solution until pH=8. The water layer was separated. Then the separated water layer was extracted with 50 ml ethyl acetate, and the organic phase was combined and washed with 150 ml water thrice, and then concentrated to obtain a dark red oily substance. The obtained dark red oily substance was recrystallized by methanol to obtain 76.25 g solid (yield: 92.0%, HPLC purity: 99.5%).

Example 8

The Preparation of 4-benzyl-1-phenethyl-piperazine-2,6-dione (the Compound of Formula IV)

To a 500 ml reaction flask 18.0 g N-benzyliminodiacetic acid (the compound of formula I) and 63.0 g acetic anhydride were added in sequence, reacted at 90° C. for 1 h, and then cooled. The reaction mixture was distilled under reduced pressure to remove the acetic acid and acetic anhydride, to obtain a dark red oily substance. The obtained dark red oily substance was cooled in ice bath, and then a mixture of 9.9 g β-phenethylamine and 160 ml toluene was added dropwise. After dropping, the ice bath was removed, and the reaction mixture was reacted at room temperature for 1 h. To the reaction mixture 30.0 g acetic anhydride and 9.8 g triethylamine were further added in sequence, and then reacted at 50° C. for 5 h. The reaction solution was cooled and 100 ml water was added. Then the reaction solution was adjusted with potassium carbonate until pH was about 8. The water layer was separated. Then the separated water layer was extracted with 50 ml toluene, and the organic phase was combined and washed with 50 ml water twice, and then concentrated to obtain a dark red oily substance. The obtained dark red oily substance was recrystallized by methanol to obtain 22.87 g solid (yield: 92.0%, HPLC purity: 99.1%).

Example 9

The Preparation of 4-benzyl-1-phenethyl-piperazine-2,6-dione (the Compound of Formula IV)

To a 500 ml reaction flask 20.9 g N-benzyliminodiacetic acid (the compound of formula I) and 76.0 g acetic anhydride were added in sequence, reacted at 90° C. for 1 h, and then cooled. The reaction mixture was distilled under reduced pressure to remove the acetic acid and acetic anhydride, to obtain a dark red oily substance. The obtained dark red oily substance was cooled in ice bath, and then a mixture of 11.5 g β-phenethylamine and 180 ml ethyl acetate was added dropwise. After dropping, the ice bath was removed, and the reaction mixture was reacted at room temperature for 1 h. To the reaction mixture 38.0 g acetic anhydride and 11.4 g triethylamine were further added in sequence, and then reacted at 55° C. for 4 h. The reaction solution was cooled and 150 ml water was added. Then the reaction solution was adjusted with potassium carbonate until pH was about 8. The water layer was separated. Then the separated water layer was extracted with 50 ml ethyl acetate, and the organic phase was combined and washed with 50 ml water twice, and then concentrated to obtain a dark red oily substance. The obtained dark red oily substance was recrystallized by methanol to obtain 26.85 g solid (yield: 93.0%, HPLC purity: 99.2%).

Example 10

The Preparation of 4-benzyl-1-phenethyl-piperazine-2,6-dione (the Compound of Formula IV)

To a 250 ml reaction flask 5.5 g N-benzyliminodiacetic acid (the compound of formula I) and 20.0 g acetic anhydride were added in sequence, reacted at 120-130° C. for 20 min, and then cooled. The reaction mixture was distilled under reduced pressure to remove the acetic anhydride, to obtain a dark red oily substance. To the obtained dark red oily substance 150 ml acetone was added and then 3.0 g β-phenethylamine was added dropwise. After dropping, the reaction mixture was stirred at room temperature for 1 h. To the reaction mixture 20.0 g trifluoroacetic anhydride and 2.4 g pyridine were further added in sequence, and then reacted under reflux for 4 h. The reaction mixture was cooled and concentrated, and then 100 ml ethyl acetate and 100 ml water were added to the residue. The reaction solution was adjusted with potassium carbonate until pH was about 8. The water layer was separated. Then the separated water layer was extracted with 50 ml ethyl acetate, and the organic phase was combined and washed with 40 ml water twice, and dried with anhydrous magnesium sulfate, filtered and concentrated, obtaining a yellow oily substance. The obtained yellow oily substance was recrystallized by methanol to obtain 7.05 g solid (yield: 92.6%, HPLC purity: 98.6%).

Example 11

The Preparation of 4-benzyl-1-phenethyl-piperazine-2,6-dione (the Compound of Formula IV)

To a 250 ml reaction flask 10.0 g N-benzyliminodiacetic acid (the compound of formula I) and 35.0 g acetic anhydride were added in sequence, reacted at 90-100° C. for 15 min, and then cooled. The reaction mixture was distilled under reduced pressure to remove the acetic acid and acetic anhydride, to obtain a dark red oily substance. The obtained dark red oily substance was cooled in ice bath, and then a mixture of 5.5 g β-phenethylamine and 150 ml ethyl acetate was added dropwise. After dropping, the ice bath was removed, and the reaction mixture was reacted at room temperature for 1 h. To the reaction mixture 8.5 g oxalyl chloride and 5.0 g triethylamine were further added in sequence, and then reacted at 60° C. for 4 h. The reaction solution was cooled and 50 ml water was added. Then the reaction solution was adjusted with saturated sodium bicarbonate solution until pH was about 8. The water layer was separated. Then the separated water layer was extracted with 50 ml ethyl acetate, and the organic phase was combined and washed with 50 ml water twice, and then concentrated to obtain a dark red oily substance. The obtained dark red oily substance was recrystallized by methanol to obtain 12.58 g solid (yield: 91.1%, HPLC purity: 98.7%).

Example 12

The Preparation of 4-benzyl-1-phenethyl-piperazine-2,6-dione (the Compound of Formula IV)

To a 250 ml reaction flask 10.0 g N-benzyliminodiacetic acid (the compound of formula I) and 35.0 g acetic anhydride were added in sequence, reacted at 90-100° C. for 15 min, and then cooled. The reaction mixture was distilled under reduced pressure to remove the acetic acid and acetic anhydride, to obtain a dark red oily substance. The obtained dark red oily substance was cooled in ice bath, and then a mixture of 5.5 g β-phenethylamine and 150 ml ethyl acetate was added dropwise. After dropping, the ice bath was removed, and the reaction mixture was reacted at room temperature for 1 h. To the reaction mixture 15.0 g triphosgene and 5.0 g triethylamine were further added in sequence, and then reacted at 60° C. for 4 h. The reaction solution was cooled and 50 ml water was added. Then the reaction solution was adjusted with saturated sodium bicarbonate solution until pH was about 8. The water layer was separated. Then the separated water layer was extracted with 50 ml ethyl acetate, and the organic phase was combined and washed with 50 ml water twice, and then concentrated to obtain a dark red oily substance. The obtained dark red oily substance was recrystallized by methanol to obtain 12.64 g solid (yield: 91.5%, HPLC purity: 98.4%).

Example 13

The Preparation of 4-benzyl-1-phenethyl-piperazine-2,6-dione (the Compound of Formula IV)

To a 250 ml reaction flask 10.0 g N-benzyliminodiacetic acid (the compound of formula I) and 35.0 g acetic anhydride were added in sequence, reacted at 90-100° C. for 15 min, and then cooled. The reaction mixture was distilled under reduced pressure to remove the acetic acid and acetic anhydride, to obtain a dark red oily substance. The obtained dark red oily substance was cooled in ice bath, and then a mixture of 5.5 g β-phenethylamine and 150 ml isopropyl acetate was added dropwise. After dropping, the ice bath was removed, and the reaction mixture was reacted at room temperature for 1 h. To the reaction mixture 11.5 g acetic anhydride and 4.0 g pyridine were further added in sequence, and then reacted at 60° C. for 4 h. The reaction solution was cooled and 50 ml water was added. Then the reaction solution was adjusted with potassium carbonate until pH was about 8. The water layer was separated. Then the separated water layer was extracted with 50 ml isopropyl acetate, and the organic phase was combined and washed with 50 ml water twice, and then concentrated to obtain a dark red oily substance. The obtained dark red oily substance was recrystallized by methanol to obtain 12.57 g solid (yield: 91.0%, HPLC purity: 99.5%).

Example 14

The Preparation of 4-benzyl-1-phenethyl-piperazine-2,6-dione (the Compound of Formula IV)

To a 250 ml reaction flask 10.0 g N-benzyliminodiacetic acid (the compound of formula I) and 35.0 g acetic anhydride were added in sequence, reacted at 90-100° C. for 15 min, and then cooled. The reaction mixture was distilled under reduced pressure to remove the acetic acid and acetic anhydride, to obtain a dark red oily substance. The obtained dark red oily substance was cooled in ice bath, and then a mixture of 5.5 g β-phenethylamine and 150 ml isopropyl acetate was added dropwise. After dropping, the ice bath was removed, and the reaction mixture was reacted at room temperature for 1 h. To the reaction mixture 11.5 g acetic anhydride and 3.36 g imidazole were further added in sequence, and then reacted at 60° C. for 4 h. The reaction solution was cooled and 50 ml water was added. Then the reaction solution was adjusted with potassium carbonate until pH was about 8. The water layer was separated. Then the separated water layer was extracted with 50 ml isopropyl acetate, and the organic phase was combined and washed with 50 ml water twice, and then concentrated to obtain a dark red oily substance. The obtained dark red oily substance was recrystallized by methanol to obtain 12.64 g solid (yield: 91.5%, HPLC purity: 99.3%).

Example 15

The Preparation of 4-benzyl-1-phenethyl-piperazine-2,6-dione (the Compound of Formula IV)

To a 250 ml reaction flask 10.0 g N-benzyliminodiacetic acid (the compound of formula I) and 35.0 g acetic anhydride were added in sequence, reacted at 90-100° C. for 15 min, and then cooled. The reaction mixture was distilled under reduced pressure to remove the acetic acid and acetic anhydride, to obtain a dark red oily substance. The obtained dark red oily substance was cooled in ice bath, and then a mixture of 5.5 g β-phenethylamine and 150 ml isopropyl acetate was added dropwise. After dropping, the ice bath was removed, and the reaction mixture was reacted at room temperature for 1 h. To the reaction mixture 11.5 g acetic anhydride and 4.0 g sodium acetate were further added in sequence, and then reacted at 60° C. for 4 h. The reaction solution was cooled and 50 ml water was added. Then the reaction solution was adjusted with potassium carbonate until pH was about 8. The water layer was separated. Then the separated water layer was extracted with 50 ml isopropyl acetate, and the organic phase was combined and washed with 50 ml water twice, and then concentrated to obtain a dark red oily substance. The obtained dark red oily substance was recrystallized by methanol to obtain 12.57 g solid (yield: 91.0%, HPLC purity: 99.2%).

The invention claimed is:

1. A compound of formula III or pharmaceutically acceptable salts thereof:

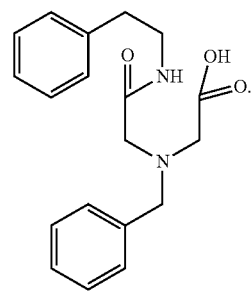

2. The compound according to claim 1, wherein the pharmaceutically acceptable salts of the compound of formula III can be selected from sulfates, hydrochlorides, phosphates, acetates, oxalates, formates, nitrates and mesylates.

3. A method for preparing the compound of formula III of claim 1, comprising the steps of:

Step 1. carrying out a dehydration reaction between a compound of formula I and acetic anhydride

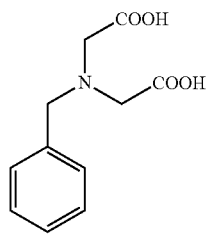

to obtain a compound of formula II

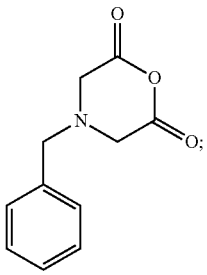

Step 2. carrying out an acylation reaction between the compound of formula II and β-phenethylamine in the presence of an aprotic organic solvent, to obtain the compound of formula III.

4. The method according to claim 3, wherein the aprotic organic solvent can be selected from ether, aromatic hydrocarbon, hydrocarbon or halogenated hydrocarbon, ester and ketone solvents, wherein the aromatic hydrocarbon solvents are selected from benzene, toluene, ethylbenzene, and dimethylbenzene; wherein the hydrocarbon or halogenated hydrocarbon solvents are selected from n-hexane, cyclohexane, n-heptane, dichloromethane, trichloromethane, and dichloroethane.

5. The method according to claim 4, wherein the ether solvent is methyl tert-butyl ether; the aromatic hydrocarbon solvent is toluene; the hydrocarbon or halogenated hydrocarbon solvents are selected from n-hexane, cyclohexane, n-heptane, dichloromethane, trichloromethane and dichloroethane; the ester solvent is ethyl acetate or isopropyl acetate; and the ketone solvent is acetone.

6. The method according to claim 3, wherein the temperature of the acylation reaction in step 2 is 5-40° C.

7. A method for preparing a compound of formula IV, comprising carrying out a cyclization reaction of the compound of formula III according to claim 1 in the presence of a dehydrating agent and an alkaline substance in an aprotic organic solvent, to obtain the compound of formula IV:

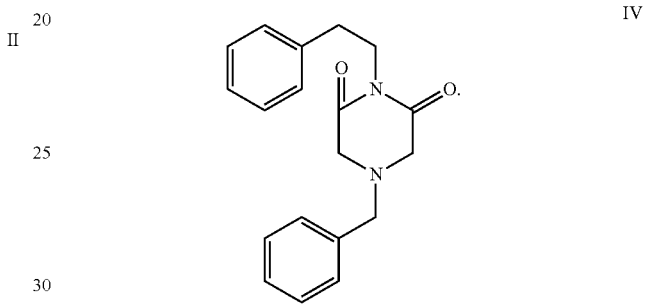

8. The method according to claim 7, wherein the dehydrating agent in the cyclization reaction is acetic anhydride.

9. The method according to claim 7, wherein the alkaline substance in the cyclization reaction is triethylamine.

10. The method according to claim 7, wherein the aprotic organic solvents are selected from acetone, methyl tert-butyl ether, toluene, ethyl acetate and isopropyl acetate.

11. The method according to claim 7, wherein the reaction temperature of the cyclization reaction is 40-80° C.

* * * * *